United States Patent
Bender

(10) Patent No.: US 8,971,491 B2
(45) Date of Patent: Mar. 3, 2015

(54) SYSTEM AND METHOD FOR IMPROVED RADIOSURGERY COLLIMATION

(71) Applicant: Wisconsin Alumni Research Foundation, Madison, WI (US)

(72) Inventor: Edward Thomas Bender, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 185 days.

(21) Appl. No.: 13/799,688

(22) Filed: Mar. 13, 2013

(65) Prior Publication Data
US 2014/0270075 A1  Sep. 18, 2014

(51) Int. Cl.
A61N 5/10 (2006.01)

(52) U.S. Cl.
CPC .................. *A61N 5/1042* (2013.01)
USPC .............................. 378/65; 378/145

(58) Field of Classification Search
CPC ........ A61N 5/1042; A61N 5/10; A61N 5/103
USPC ................. 378/64–65, 145–147
See application file for complete search history.

(56) References Cited

U.S. PATENT DOCUMENTS

| | | | |
|---|---|---|---|
| 5,317,616 A | 5/1994 | Swerdloff et al. | |
| 6,385,286 B1 | 5/2002 | Fitchard et al. | |
| 6,580,940 B2 * | 6/2003 | Gutman | 600/427 |
| 2001/0044574 A1 * | 11/2001 | Warne et al. | 600/407 |
| 2010/0054409 A1 * | 3/2010 | Bose et al. | 378/65 |
| 2011/0026682 A1 * | 2/2011 | Oosting | 378/145 |

OTHER PUBLICATIONS

Ahnesjo, et al., A Pencil Beam Model for Photon Dose Calculation, Med. Phys., 1992, 19:263-273.
Sharpe, et al., Compensation of X-ray Beam Penumbra in Conformal Radiotherapy, Med. Phys., 2000, 27 (8):1739-1745.

* cited by examiner

*Primary Examiner* — Hoon Song
(74) *Attorney, Agent, or Firm* — Quarles & Brady, LLP

(57) ABSTRACT

A system and method is provided for radiation system collimation and design. A plurality of channel waveguide assemblies are provided to be operatively associated with respective beam collimators having varying longitudinal bore diameters. The plurality of channel waveguide assemblies includes a plurality of guides and concentric spacers. The plurality of guides and concentric spacers include varying inner diameters that are configured to be securably nested together by decreasing inner diameters and secured within the longitudinal bores of the respective beam collimators.

20 Claims, 9 Drawing Sheets

SYSTEM AND METHOD FOR IMPROVED RADIOSURGERY COLLIMATION

CROSS-REFERENCE TO RELATED APPLICATIONS

N/A

STATEMENT REGARDING FEDERALLY SPONSORED RESEARCH

N/A

BACKGROUND OF THE INVENTION

The field of the invention is medical devices. More particularly, the invention relates to medical devices applicable to radiosurgery.

Radiosurgery is a non-invasive medical procedure that ablates a targeted tissue by ionization of targeted cells with high-energy beams of radiation. The ionization process causes ions and free radicals to be released within the target cells and ultimately results in cell death. As such, it is important that the irradiation is directed only to targeted cells, such as tumors or other targeted cell masses. Commonly, however, healthy tissue surrounding the target cells are damaged in the process due to various difficulties of existing technology that are identified as follows.

Linac-based stereotactic radiosurgery involves ejecting a beam of electrons from an electron gun and delivering an acceleration energy to the electrons in the form of microwaves. The electrons subsequently impact a metal target, producing x-rays. In some linac-based systems, the highly energized electron beam is redirected by application of magnetic fields before striking the target, and the resulting x-rays travel toward a modification center where the beam is treated prior to delivery to the target cells. A common modification process involves colliding the beam by placement of a collimator interrupting the beam pathway such that an opening in the collimator allows for passage of only radiation that is directed towards the intended target. A secondary collimator placed downstream provides further refinement in shaping the beam by absorbing x-rays as required. Radionuclide based radiosurgery is similar, with the exception that instead of electrons striking a metal target to produce x-rays, naturally occurring x-rays from the radionuclide, typically $^{60}$Co, act as the radiation source. Beam modification as described above then proceeds in an analogous manner as with linear accelerator based radiosurgery.

Generally, two classes of collimators are available for application in the linac-based system, including circular cone collimators and multileaf collimators. Typically, the circular cones are used for lesions in the 4 mm to 30 mm range, while the multileaf collimators are preferred for larger or more complex lesions that would require a complex radiation beam shape that is achievable by dynamic positioning of the metal leaflets during treatment. The multileaf collimator, however, is limited to a more shallow penumbra and more gradual dose falloff around the target. On the other hand, the circular cones are able to achieve a steeper dose falloff and thereby spares more of the surrounding healthy tissue. What is needed in the standard conical collimator is a means for increasing both the dose gradient and dose uniformity in the radiosurgery process.

In stereotactic radiosurgery of lesions in a brain, precisely directed radiation is very important. With the so-called Gamma Knife system, several radioactive sources surround a patient's skull with a specialized collimator placed between the sources and the skull. The radiation beams that pass through the collimator converge at a predetermined point inside the patient. For instance, a radioactive cobalt source may emit a plurality of gamma rays directed toward a helmet surrounding the patient's skull, whereby the rays are collided by the helmet such that only certain rays having a common delivery point are delivered to the patient's skull. Stereotactic radiosurgery systems typically utilize circular cone collimators for modifying the emitted rays.

Since any damage to healthy brain tissue may have undesired health implications, the irradiation is highly selective and the dose gradient beyond the edges of the radiation field is a key concern during treatment planning phases of stereotactic radiosurgery. Typically, the volume of brain receiving a certain dose, such as 12 Gy, is monitored as a plan quality metric since such dosimetric parameters have been correlated to toxicities. Alternatively, a dose gradient index can be determined as the ratio of the volume receiving 50% of the prescription dose to the volume receiving the full prescription dose. This plan quality metric has been correlated to toxicities, for example in radiosurgery for meningioma. Additionally, the homogeneity of the dose distribution inside the target, as measured by the maximal point dose, or as an integrated dose to a clinically relevant sub-volume of the target, has been correlated to toxicities after treatment for benign diseases such as vestibular schwanoma and meningioma with stereotactic radiosurgery. Given the above two examples of clinical correlates in the plan quality metrics, what is needed is a technological development that provides an increase in dose gradient and/or an increase in dose homogeneity for improving patient care in stereotactic radiosurgery.

In general, there are two main considerations that influence the penumbra and uniformity in the dose distribution for conical collimator based radiosurgery. First, the radiation source is not truly a point source and therefore is amenable to blurring in the dose distribution. Blurring may be minimized by placement of the collimator as close as possible to the target volume. Second, the transport of secondary electrons and scattered photons away from a primary interaction point leads to additional blurring in the dose distribution. Both of these two physical phenomena can be incorporated into a pencil beam dose calculation formalism. Given that these phenomena are relatively well characterized in regard to prior knowledge of the shape of the effective dose kernel, a fluence pattern could theoretically be designed to optimize both dose gradient and uniformity. Sharpe et al. (M. B. Sharpe, B. M. Miller and J. W. Wong, "Compensation of x-ray beam penumbra in conformal radiotherapy," Med Phys 27, 1739-1745 (2000).) have developed a technique for increasing dose gradient for larger fields using modulation by introducing a larger fluence at beam edges. The technique of Sharpe et al., however, considered larger fields that were sized for use in conventional lung radiotherapy, and further, the optimal size and intensity of the additional fluence at beam edge was arrived at empirically. What is needed is a method addressing smaller fields having an optimized fluence distribution.

Therefore, it would be desirable to have a system and method to address the above concerns and to provide related advantages.

SUMMARY OF THE INVENTION

The present invention overcomes the aforementioned drawbacks by providing a system and method for increasing both a dose gradient and a dose uniformity that is achieved with a conical collimator. Specifically, the present invention includes a system and method for providing a channel waveguide assembly comprising nestable cylinders configured to be mounted relative to the conical collimator.

In accordance with one aspect of the present invention, a radiosurgery system is disclosed that includes a patient table configured to receive a patient thereon, a radiation source comprising an exit orifice configured to emit a beam of radiation along a path extending from the exit orifice toward the patient table to perform radiosurgery on the patient, and a beam collimator arranged with the path and forming a longitudinal bore extending along the path from an inlet and an outlet. A channel waveguide assembly is secured to extend along the path to control a portion of the beam of radiation directed through the longitudinal bore of the collimator, the channel waveguide assembly. The channel waveguide assembly includes a first hollow guide having an inlet orifice and outlet orifice to form a first guide passage through the first hollow guide and defining a first guide inner diameter and a first guide outer diameter, wherein the first guide outer diameter corresponds to the longitudinal bore of the beam collimator. The channel waveguide assembly also includes a second hollow guide having an inlet orifice and outlet orifice to form a second guide passage through the second hollow guide and defining a second guide inner diameter and a second guide outer diameter, wherein the second guide outer diameter is less than the first guide diameter by a predetermined value. The channel waveguide assembly further includes at least one concentric spacer received around the second hollow guide and having a radial structure configured to correspond to the predetermined value to secure the second hollow guide within the first hollow guide and, thereby, form the channel waveguide configured to constrain the portion of the beam of radiation directed along the path and through the longitudinal bore.

In accordance with another aspect of the invention, a system for retrofitting a beam collimator is disclosed that includes a plurality of channel waveguide assemblies configured to be operatively associated with respective beam collimators having varying longitudinal bore diameters. The plurality of channel waveguide assemblies further includes a plurality of hollow guides and concentric spacers, wherein the plurality of hollow guides and concentric spacers comprise varying inner diameters that are configured to be securely nested together by decreasing inner diameters and secured within the longitudinal bores of the respective beam collimators.

In accordance with another aspect of the invention, a method for providing a channel waveguide assembly for a beam collimator is provided that includes computing a desired fluence distribution to produce a dose distribution that approximates a top-hat distribution within a desired tolerance, wherein computing the desired fluence distribution includes reducing a sum of squared difference between a calculated dose distribution and a top-hat distribution by adjusting the fluence distribution. The method also includes computing a desired fluence distribution of a solid compensator to reproduce the desired fluence distribution, wherein computing the desired fluence distribution of the solid compensator includes reducing a sum of squared differences between the desired fluence distribution and a calculated fluence distribution of the solid compensator. The method further includes adjusting a design of the solid compensator by changing a one-dimensional function of the solid compensator and selecting at least one of a plurality of variably-sized guides according to the desired design of the solid compensator, the at least one guide configured to be nested within a longitudinal bore of the beam collimator such that the combination of the nested guides and beam collimator produces the desired dose distribution at a target location when a radiation beam is collided.

In accordance with yet another aspect of the invention, a method for creating a collimation system for a radiation system is disclosed that includes determining a set of outer diameter measurements and a set of heights for a plurality of guides. The determination includes identifying a plurality of inner diameter sizes of a multitude of beam collimators having varying inner diameter sizes, identifying a plurality of cylindrical heights of a multitude of beam collimators, and creating the set of outer diameter measurements for the plurality of guides, the set of outer diameter measurements having smaller diameters that are configured to be received through the inner diameters of the multitude of beam collimators. The method also includes creating the set of cylindrical heights for the plurality of guides, the set of cylindrical heights comprising at least one height that is equal to an identified height in the multitude of beam collimators and manufacturing a plurality of guides with dimensions corresponding to the determined set of outer diameter measurements and the set of cylindrical heights. The method further includes manufacturing a plurality of concentric spacers having inner diameters corresponding to the set of outer diameter measurements of the plurality of guides and manufacturing a plurality of concentric spacer having outer diameters corresponding to the identified plurality of inner diameter sizes of the multitude of beam collimators.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

The following definitions and terms are provided to clarify the description of the present invention and to guide those of ordinary skill in the art in the practice of the present invention.

As used herein, the term "radiosurgery" refers to the treatment of a patient through the application of radiation to a target region. As used herein, the term "radiation" includes electrons; x-rays and other photons; neutrons; protons; and heavy charged particles, such as elemental ions.

The succeeding description of the invention is made with respect to stereotactic radiosurgery systems that employ conical-based collimators. For example, stereotactic radiosurgery systems such as the CyberKnife® system (Accuray, Sunnyvale, Calif.), traditional gantry-mounted linear accelerator ("linac") systems, and Gamma Knife® system (Elekta, Stockholm, Sweden) can utilize the present invention, in addition to any other radiation therapy systems having conical-based collimators. It will be appreciated by those skilled in the art that therapeutic x-rays, gamma rays, or other forms of radiation may be utilized in the present invention.

Figure 1:
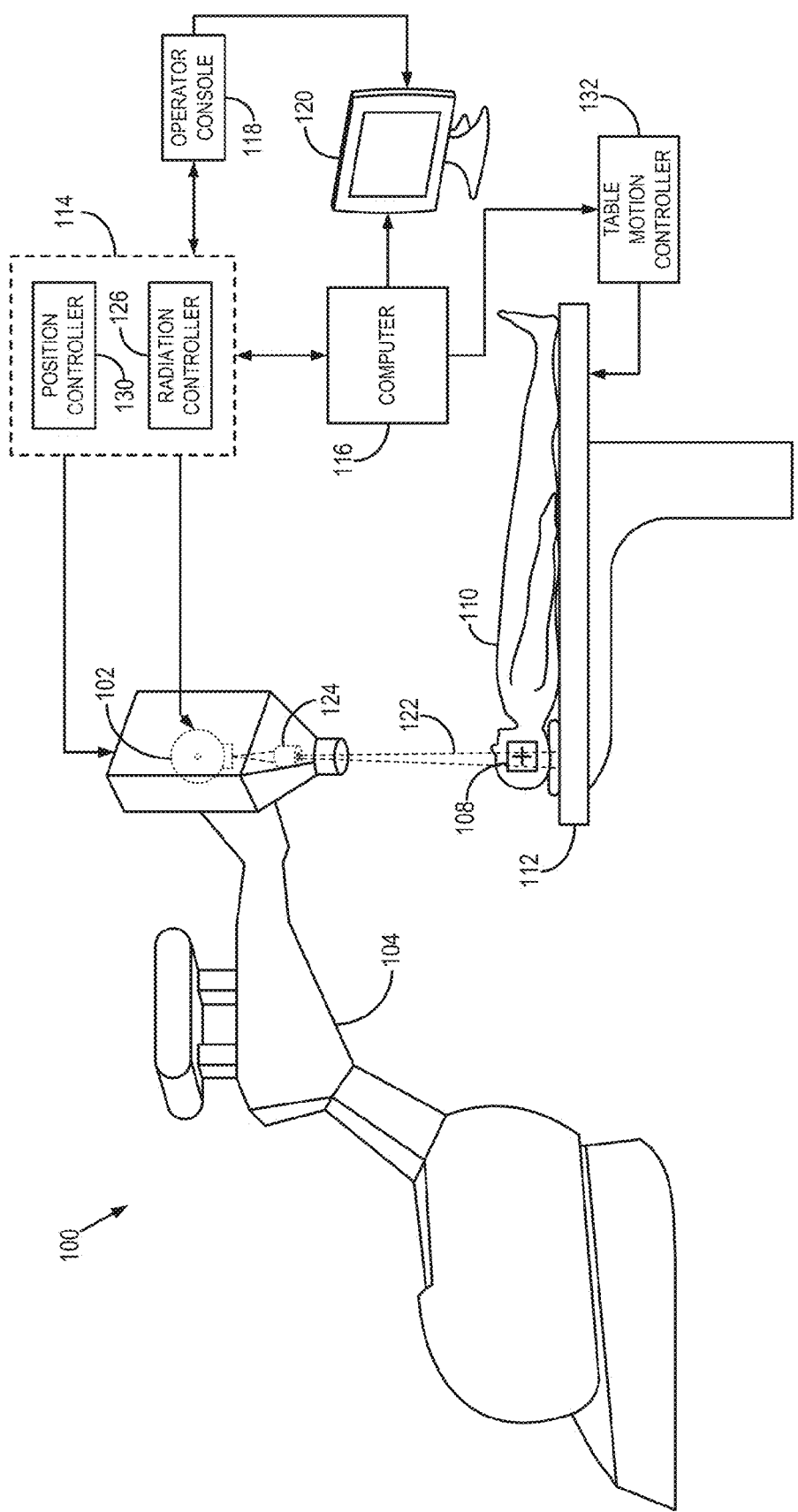
FIG. 1 is a perspective view of a linac-based radiation therapy system in accordance with the present invention.

Referring to FIG. 1, an example of a linac-based radiation therapy system 100 that may be used when practicing the present invention includes a radiation source 102, such as a linear accelerator, that is housed at an end of rotatable arm 104. The rotatable arm 104 allows the radiation source 102 to be aligned in a desired manner with respect to a target volume 108 in a subject 110 positioned on a patient table 112. A control system 114 controls the rotation of arm 104 through position controller 130 and the delivery of radiation from the radiation source 102 to the target volume 108 with a radiation controller 126. The system 100 includes a computer 116 that receives commands and scanning parameters from an operator via a operator console 118, or from a memory or other suitable storage medium. An associated display 120 allows the operator to observe data from the computer 116 or operator console 118, including images of the subject 110 that may be used to review or modify the treatment plan, and to position the subject 110 by way of appropriately adjusting the position of the patient table 112 with a table motion controller 132. The operator supplied commands and parameters may also be used by the computer 116 to provide control signals and information to the control mechanism 114.

The radiation source 102 produces a radiation beam 122, or "field," that is modulated by a collimator 124. The collimator 124 may include a conical-based collimator that comprises a bore extending through its center. In such a configuration, the collimator 124 is composed of an appropriate material that inhibits the transmission of radiation, such as a dense radioopaque material, and may include lead, tungsten, cerium, tantalum, or related alloys.

During use, the radiation source 102 rotates so that the radiation beam 122 may irradiate the target volume 108 in the subject 110 from a variety of radiating angles. Specifically, the radiation source 102 is controlled by the radiation controller 126 that provides power and timing signals to the radiation source 102.

As the collimator 124 of the system 100 directs the radiation beam 122 to the target volume 108, a dose falloff around the target volume 108 may be blurred and the dose distribution may not be uniform. For instance, due to the variety of radiating angles, healthy tissue surrounding the target volume 108 may be irradiated, the radiation beam 122 may be partially diffused, and the radiation beam edges may be blurred around the periphery of the target volume 108 due to the distance that must be traveled by the x-rays from the radiation source 102 to the target volume 108. The present invention provides a system and method to sharpen the radiated beam and improve its dose uniformity by optimizing function of the collimator 124 with fluence modulation as described in the succeeding paragraphs.

Fluence Modulation Theory and Method

In a pencil beam model for dose calculation, the 2-D dose distribution in a patient, D(r), due to a 2-D radiation fluence distribution, F(r), can be calculated as:

$$D(\vec{r})=F(\vec{r}) \otimes K_S(\vec{r}) \otimes K_E(\vec{r}) \qquad (1).$$

In equation (1), a source kernel $K_S$ describes the distribution of the radiation source. An electron and photon scattering kernel $K_E$ describes the distribution of the radiation dose due to transport of secondary electrons and secondary photons, with the former having a predominant effect. The source kernel $K_S$ is modeled as a two-component Gaussian distribution, while the electron and photon scattering kernel $K_E$ is modeled after Monte-Carlo data available in the literature5. Due to the circular symmetry of the collimator 124, the dose distribution at a given depth can be described by a single function of the radius r away from an isocenter of the beam in a direction perpendicular to a line connecting the source and the isocenter. As the radiation delivery is arranged from a variety of beam angles coincident at the isocenter, the 3-D dose distribution can be calculated given the 2-D dose distributions described above and a selected beam arrangement. For computational efficiency, however, the collimator design is optimized in 2-D, since there is a 1:1 correspondence of both the dose gradient (i.e. falloff away from the target) and the dose uniformity within the target in the 2-D representation. An alternative formulation of equation (1) can be arrived at by modeling an extended source as a set of N point sources. This formulation is not susceptible to errors associated with source occlusion, and may be more generally applicable to larger radiation sources such as a $^{60}$Co source.

$$D(r)=\Sigma_{i=1}^{N}F_i(r) \otimes K_E(r) \qquad (2);$$

where $F_i$ represents the fluence from element i of a set of N sub-sources. In this formulation, the fluence source may be off of the central axis of the beam, and this must be taken into account in the calculation.

Waveguide Optimization

Figure 2:
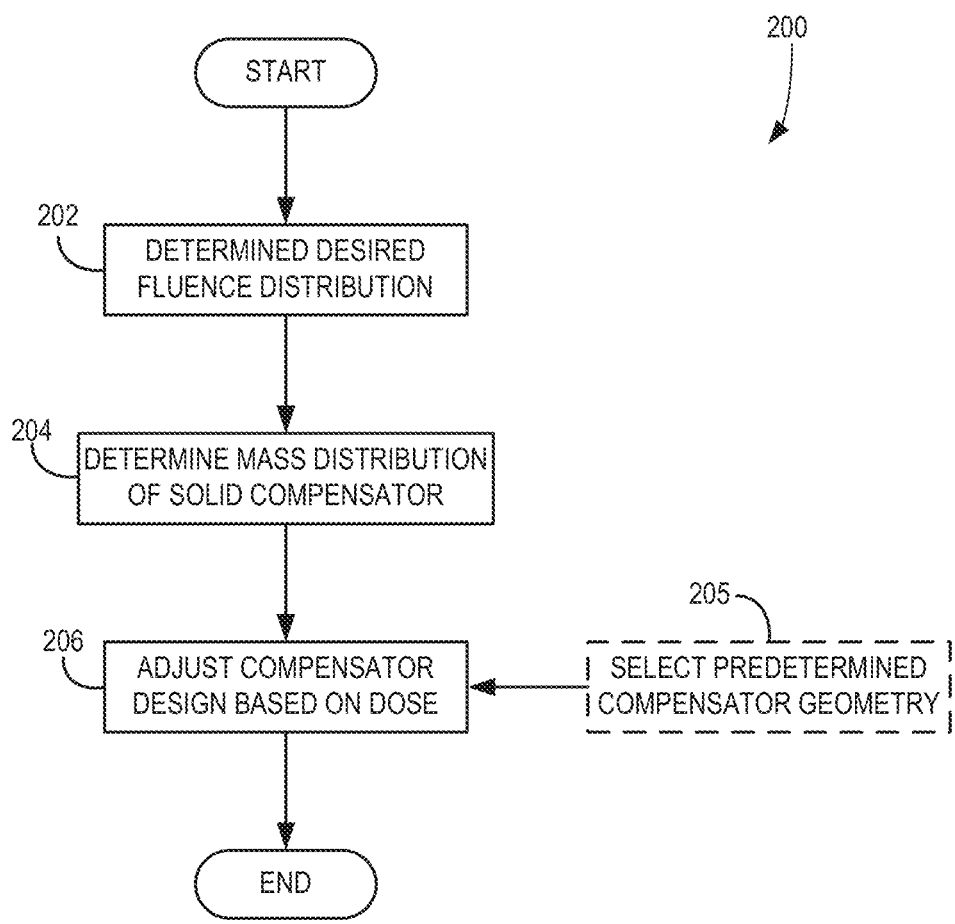
FIG. 2 is a flow chart setting forth exemplary steps of a method for designing a channel waveguide in accordance with the present invention.

Given the equation (1) above, the fluence distribution F(r) can be optimized to produce a dose distribution D(r) that best approximates a "top-hat" distribution, i.e. 100% inside the circular target and 0% outside. Since the fluence distribution cannot be controlled directly, modulation is provided with a compensator for optimizing the fluence distribution. Referring to FIG. 2, a multi-step process 200 described herein may be utilized to perform design a system to compensate for the collimator 124 or redesign the collimator 124 itself.

First, at process block 202, a desired fluence distribution F(r) is determined, such by using optimization tools provided in Matlab software (Math Works, Natik, Mass.). For example, a sum of squared differences between the calculated dose distribution D(r) and a "top-hat" distribution may be computed and minimized by adjusting the fluence distribution F(r). A penalty can be introduced to avoid solutions with low integrated fluence and nominally aim at maintaining at least 50% of the integrated photon fluence as compared to the same open field.

At process block 204, after the optimized fluence distribution F(r) is determined at process block 202, a mass distribution of a solid compensator C(r) that is capable of reproducing the optimized fluence distribution F(r) is determined. For example, a constraint may be imposed such that the thickness of the compensator across a radial profile is a unique function and one end of the compensator is forced flat. Such a constraint prevents the appearance of "voids" in the compensator that would complicate manufacturing and reduces the computational burden by uniquely describing the compensator with a one-dimensional function. This and other constraints can be adjusted, for instance relaxed, in more advanced, divergent designs. A beam divergence is taken into account when calculating the transmission of photons through the compensator as a function of radial distance r from the isocenter. The sum of squared differences between the optimized fluence distribution F(r) from step one above and the fluence calculated for the physical compensator C(r) is minimized during this step.

After a desired compensator design is determined at step 204, the compensator design may be adjusted based on dose rather, than fluence. For example, the sum of squared differences between the calculated dose distribution D(r) and a top-hat distribution may be minimized by adjusting the compensator design C(r). It is noted that this step may be the most computationally intensive and, in fact, may be performed without the preceding steps; however, the number of adjustment iterations required at process block 206 can be substantially reduced when process blocks 202 and 204 precede process block 206.

As an alternative to process blocks 202 and 204, an optimization based on a predetermined compensator architecture may be used. For example, instead of performing the steps associated with process blocks 202 and 204, a predetermined compensator geometry, such as a series of hollow cylinders or cones, can be selected at process block 205. Specifically, the diameters of hollow cylinders may be determined and the length and location of a selection of hollow cylinder sizes may be selected to best reproduce the optimal fluence pattern identified with respect to process block 202 above. This set of lengths and locations can be arrived at by minimizing the sum of squared difference between the resultant dose distribution and a "top hat" distribution. Alternatively, the sum of squared difference between the optimized fluence arrived at in block 202 and the fluence resulting from a given arrangement of the heights and locations of the hollow cylinders can be minimized. The size of the hollow cylinders can be either selected by the user or by an algorithm, with the computational time of the former may be significantly lower than the latter.

As stated above, the geometry may include multiple tapered cylinders or cones designed to achieve a design having multiple field sizes. In this configuration, the tapered hollow cylinders or cones can be placed closer to the radiation source, that is, between the radiation source 102 and the collimator 124, such that the optimized hollow cylinder arrangement and collimator 124 are mechanically independent. By forcing the same hollow cylinder design to be used for a set of cone sizes, one can arrive at a single nesting arrangement that works for a pre-defined set of collimator sizes, so that standard circular collimators can be changed without the need to move the waveguide during a treatment delivery that utilizes multiple field sizes.

An Exemplary Embodiment of a Stereotactic Radiosurgery Collimation Device

Figure 3:
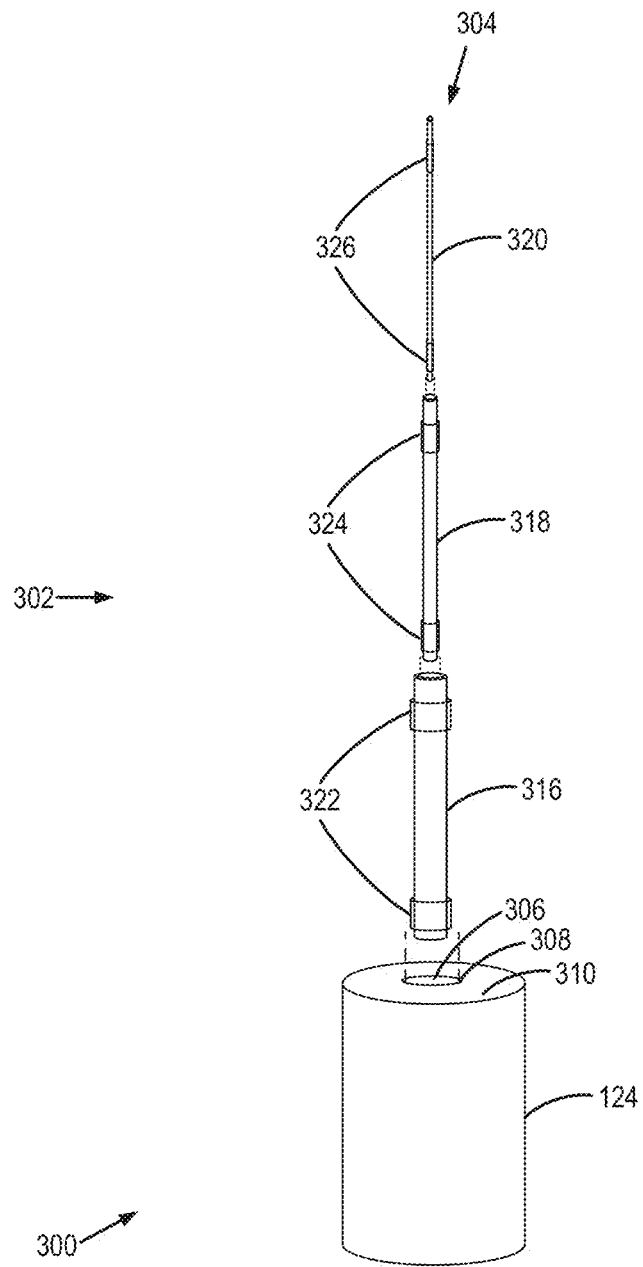
FIG. 3 is an exploded view of a beam collimator and channel waveguide assembly in accordance with the present invention.

Referring now to FIG. 3, one example of a stereotactic radiosurgery collimation device 300 in accordance with the present invention includes a beam collimator 124 and a channel waveguide assembly 302 formed by a plurality of nested waveguides 304. The channel waveguide assembly 302 is designed in accordance with the design process described above with respect to FIG. 2.

As shown in FIG. 3, the beam collimator 124 may be a standard or nonstandard cylindrical collimator configured to collide a radiation beam directed to it. Specifically, as illustrated in FIG. 1, the collimator 124 is designed to be placed proximal to an exit orifice of a radiation source 102 to interrupt a path of an emitted radiation beam 122, such that a longitudinal bore 306 extending through the collimator 124 is coaxial or approximately parallel with the path of the beam 122. The longitudinal bore 306 defines a first opening 308 on a first surface 310 of the collimator 124 and a similar, second opening on a second surface (hidden) of the collimator 124 that opposes the first surface 110. Merely by way of example, the longitudinal bore 306 may be sized at various diameters, such as 4 mm inner diameter for a smaller bore 306 and up to, for example, 18 mm inner diameter for a larger bore 306. The collimator 124 may be manufactured from dense metals, such as lead, capable of absorbing all but the radiation passing through the longitudinal bore 306.

Still referring to FIG. 3, the channel waveguide assembly 302 includes the plurality of nested waveguides 304. In this example, the plurality nested waveguides 340 include a first, a second, and a third hollow cylinder 316, 318, 320, respectively. The nested waveguides 304 may be configured to be nested by decreasing diameter and even sized to be arranged within the longitudinal bore 306 of the collimator 124. Alternatively, as will be explained, the plurality of nested waveguides 304 may be mounted along the beam path in line with but not within the longitudinal bore 306 of the collimator 124.

Each hollow cylinder 316, 318, 320 is secured into a nesting position with a corresponding pair of concentric spacers 322, 324, 326, respectively, that may, for example, frictionally secure the channel waveguide assembly 302 together. In particular, the second and third concentric spacer pairs 324, 326 may have outer diameters configured to friction fit within the inner diameters of the first and second cylinders 318, 316, respectively, while the first concentric spacer pair 322 may include an outer diameter configured to be friction fitted against the inner diameter of the longitudinal bore 306. Of course, if the waveguide assembly 302 is designed to be located proximate to instead of within the longitudinal bore 306 of the collimator 124, the first concentric spacer pair 322 may be omitted.

The hollow cylinders 316, 318, 320 may have differing lengths and may be manufactured from dense materials that are configured to sufficiently absorb any impinging radiation beams, such as stainless steel, lead, and the like. The concentric spacer pairs 322, 324, 326 may be manufactured from radiation transparent material, including aluminum, rubbers, plastics, and the like, and may be permanently affixed or removably received on an outer diameter surface of its corresponding cylinder 316, 318, 320.

In regard to FIG. 3, it is noted that although the channel waveguide assembly 302 is illustrated with three nested cylinders 316, 318, 320, any number of cylinders may be utilized in the nesting arrangement such that the optimized compensator design determined according to the method described above is achieved. Furthermore, any or all of the hollow cylinders 316, 318, 320 may be tapered such that one end of the hollow cylinder has a smaller inner diameter than a second end of the hollow cylinder. It is contemplated that such tapering may compensate for beam divergence. In a further aspect, although one pair of concentric spacers 322, 324, 326 is contemplated per cylinder 316, 318, 320, it is noted that any number of concentric spacers per cylinder may be provided such that the corresponding cylinder contained within the spacer or spacers is securably fixed in the nesting arrangement.

Figure 4A:
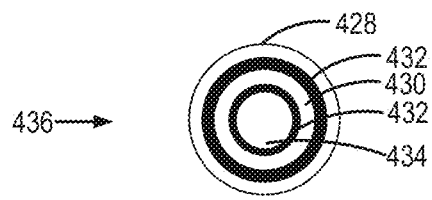
FIGS. 4A-4C illustrate top views of various channel waveguide assemblies in accordance with the present invention.
Figure 4B:
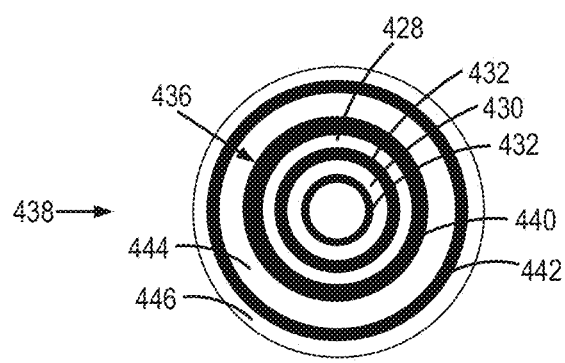
Figure 4C:
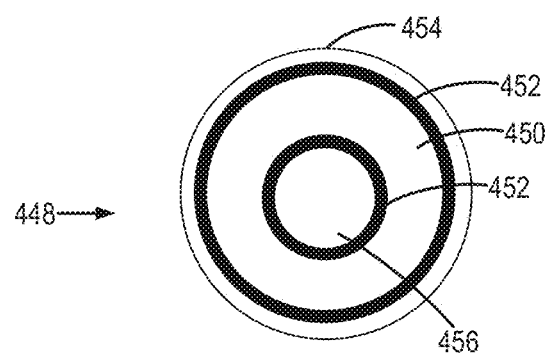

Turning now to FIGS. 4A-4C, exemplary plan views are shown for various channel waveguide assemblies 302 configured for different sized longitudinal bores 306 are shown. For example, FIG. 4A shows one embodiment of a smaller channel waveguide assembly 436 comprising an outer spacer 428 to be disposed against the longitudinal bore 406, one intermediate spacer 430 stationed between two hollow cylinders 432, and a hollow channel 434. The two hollow cylinders 432 are nested together and may have varying wall thickness and longitudinal wall lengths. In a different aspect, the spacer 430 may be compressed between the longitudinal walls.

Turning now to 4B, the above-described channel waveguide assembly 436 may be further nested within additional hollow cylinders 440, 442 separated by further spacers 444 and 446 to form a larger channel waveguide assembly 438 that may be received in larger-sized longitudinal bores 306.

On the other hand, referring to FIG. 4C, another channel waveguide assembly 448 is illustrated having relative proportions that are substantially different. The channel waveguide assembly 448 includes a notably thicker intermediate spacer 450 between two hollow cylinders 452 and a thinner outer spacer 454 and providing an inner passage 456. It is contemplated that the thicknesses of the spacers 450, 454 and the hollow cylinders 452 may vary in any manner in order for the dose distribution produced with the modified collimator to reach the desired distribution.

Figure 5:
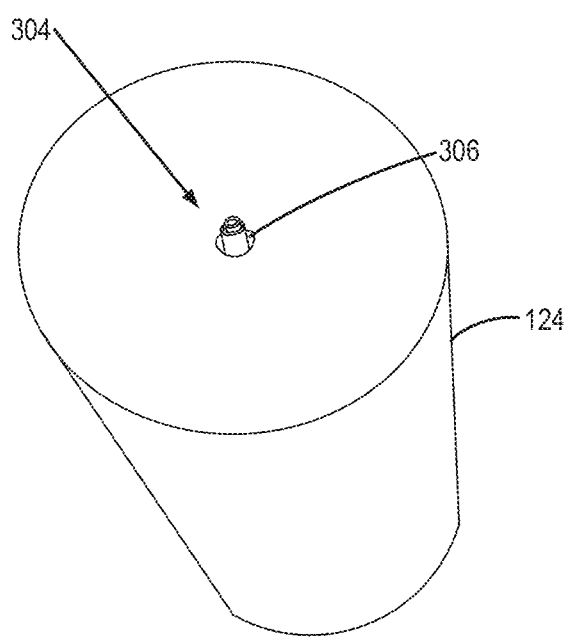
FIG. 5 is a top perspective view of a channel waveguide assembly inserted within a collimator in accordance with various embodiments of the present invention.

Turning now to FIG. 5, a top perspective view of the channel waveguide assembly 304 is provided to show the channel waveguide assembly 304 nested within the longitudinal bore 306 of the beam collimator 124. It should be noted that placement of any or all of the components in the waveguide assembly 304 may extend beyond the longitudinal bore 306, be flush with the edge of the bore 306, or recessed within the bore 306.

Figure 6:
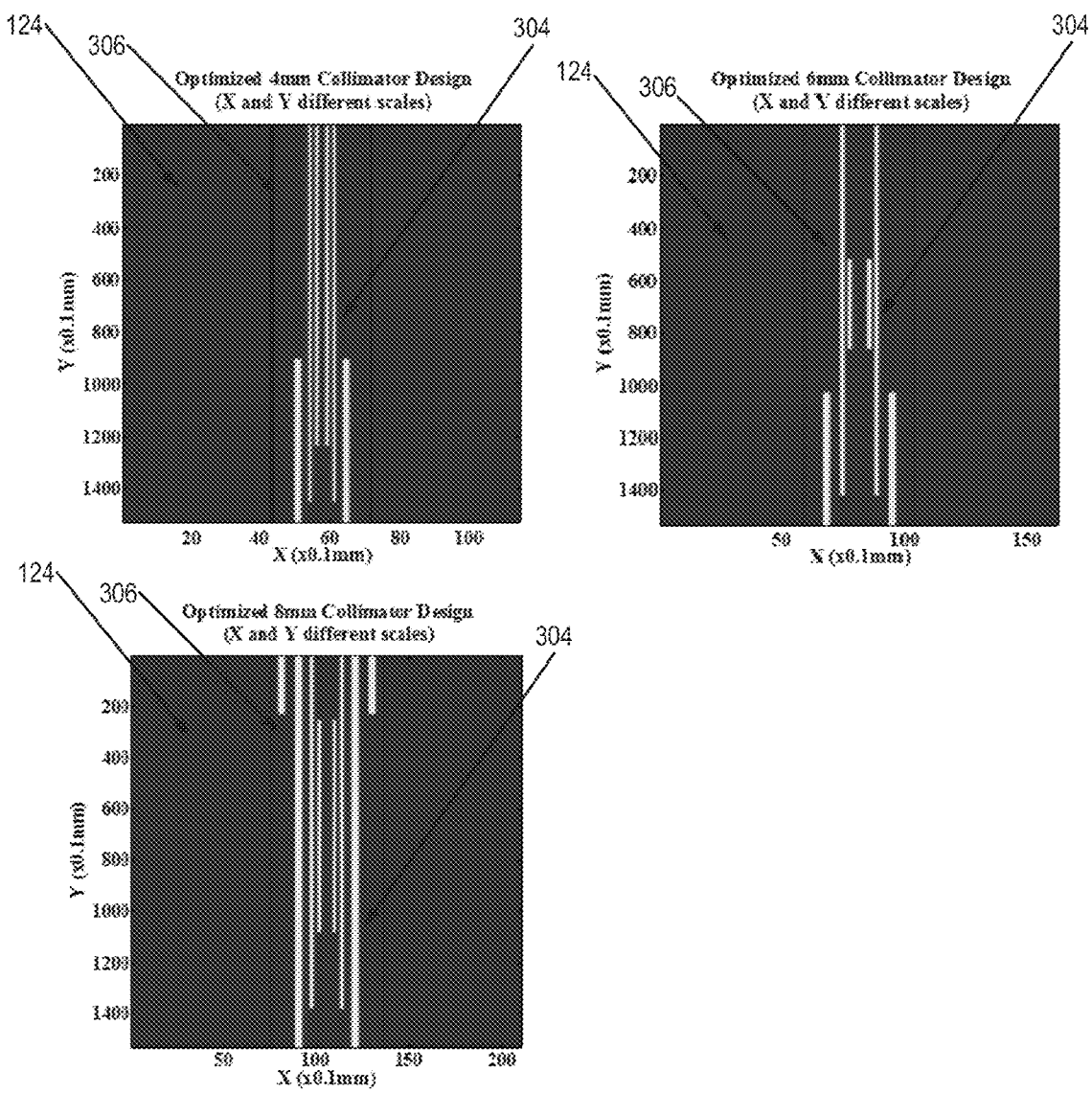
FIG. 6 is a graphical representation of collimators in accordance with the present invention.

Referring to FIG. 6, various collimator designs having various channel waveguide assemblies received therein are shown and may be indicative of cross-sectional views of modified collimators. In particular, each collimator 124 includes a longitudinal bore 306 having received therein a channel waveguide assembly 304 designed according to the optimization techniques described above. For instance, the 4 mm collimator may be optimized with hollow cylinder tubing sizes at 16, 21, and 26 gauge, the 6 mm collimator optimized with 11, 16, and 20 gauge hollow cylinders, and for the 8 mm collimator optimized with 6, 10, 15, and 19 gauge hollow cylinders.

As will be evidenced further below, the above-description provides a system and method for the conical collimator to achieve a sharper dose falloff around a radiosurgical target volume and a more uniform dose distribution inside the target volume. Particularly, a channel waveguide assembly provided for use in a radiosurgery device for delivering precision radiation doses in stereotactic conical collimator-based radiosurgery. The present invention utilizes fluence modulation to adjust the intensity of the radiation delivered to an irradiation zone. Benefits include a significant reduction of spillage radiation of nontargeted tissue. Furthermore, the improved dose gradient and dose uniformity are quality metrics with significant implications in the assessment of enrolling a patient in radiosurgery treatment. The present invention aids in the evaluation procedure by providing a more accurate treatment plan.

Prototype and Measurements

In a test of the methods described above, multiple devices were designed for circular collimators of 4 mm and 6 mm diameter. A pattern of rings was selected based on the fluence distribution F(r) of a simple design. The pattern of rings was achieved by inserting specifically sized concentric cylinders having stainless steel shafts inside a standard conical collimator that acts as a "binary" fluence modulator. The hollow cylinders were provided by hypodermic needs, which served the objective of being precisely sized, straight, and commercially available with sufficient density to absorb and shield most of the incoming fluence emitted from the radiation source. The concentric shafts of the hypodermic needles were spaced with a spacing material such that their nesting arrangement resulted in a pattern of rings that can approximate a numerically optimized fluence profile. For example, in one configuration, the spacing material was transparent tape.

Dose measurements were performed with EBT3 radiochromic film. An Epson 10000XL scanner was used, and a linear dose calibration curve was determined for each set of measurements. In order to extract profiles through the measured planar dose distributions, a two-step process was developed to detect the center of the dose distribution and subsequently extract beam profiles. First, the center of the planar dose distribution was determined as the centroid of the circular region defined by the 50% isodose line. During this step, any voids within a given field resulting from noise in the scanned image, were removed. Similarly, small isolated regions misidentified as representing over 50% isodose, due to the appearance of dust and imperfections in the film, were removed. Finally, 200 dose profiles that passed through the centroid were extracted and averaged. The averaging effectively reduces noise without smoothing requirements.

Test Results and Discussion

Figure 7:
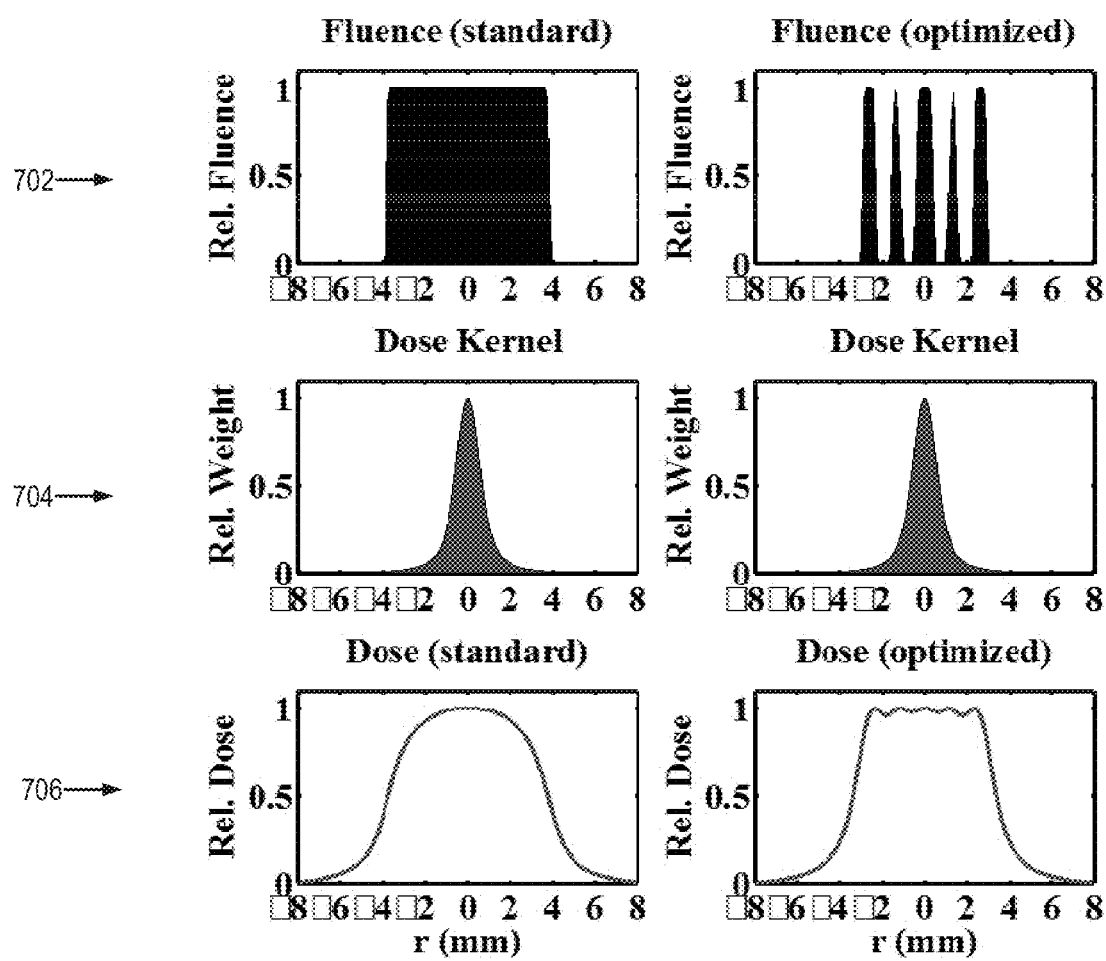
FIG. 7 is a graphical representation of examples of standard and optimized fluence and dose distributions in accordance with the present invention.
Figure 8:
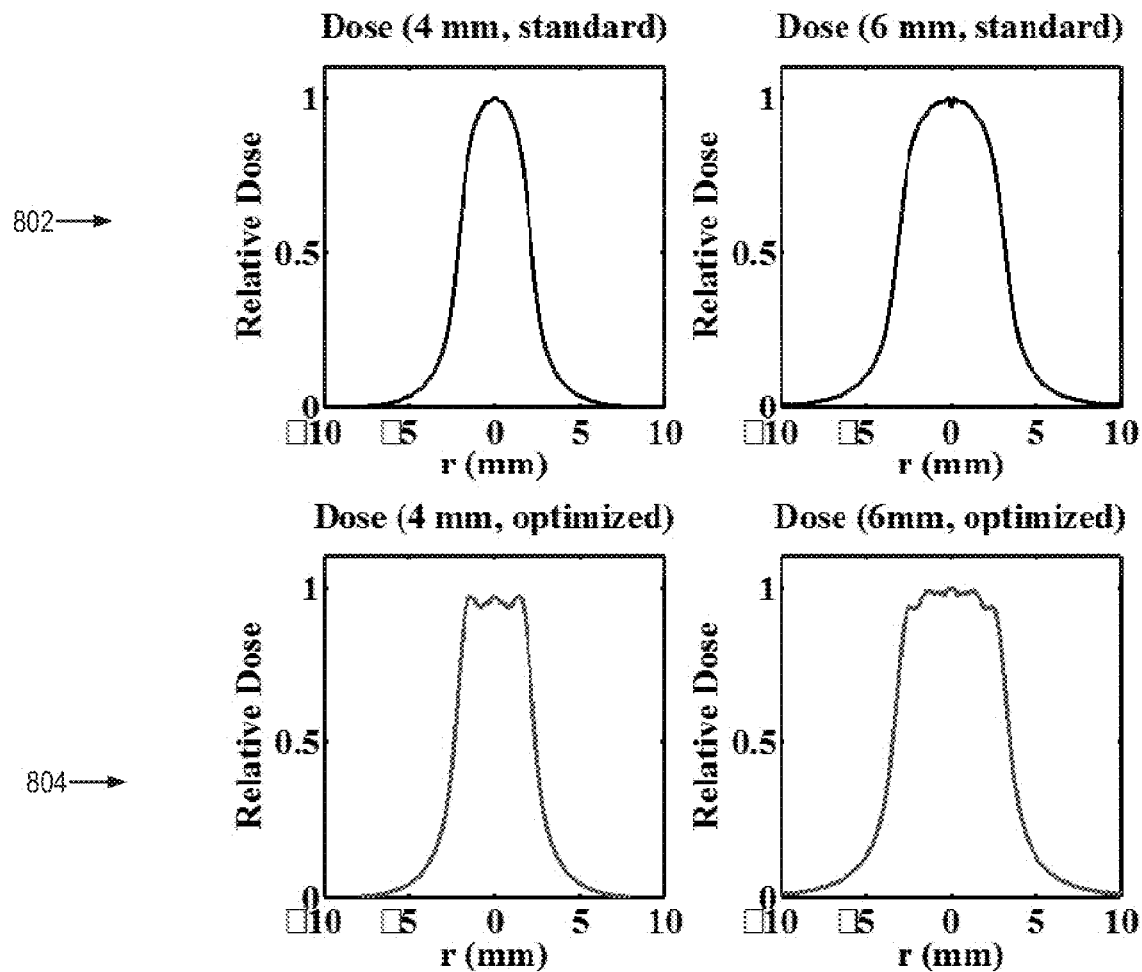
FIG. 8 is a graphical representation of measured dose distributions of standard and modified collimators in accordance with the present invention.
Figure 9:
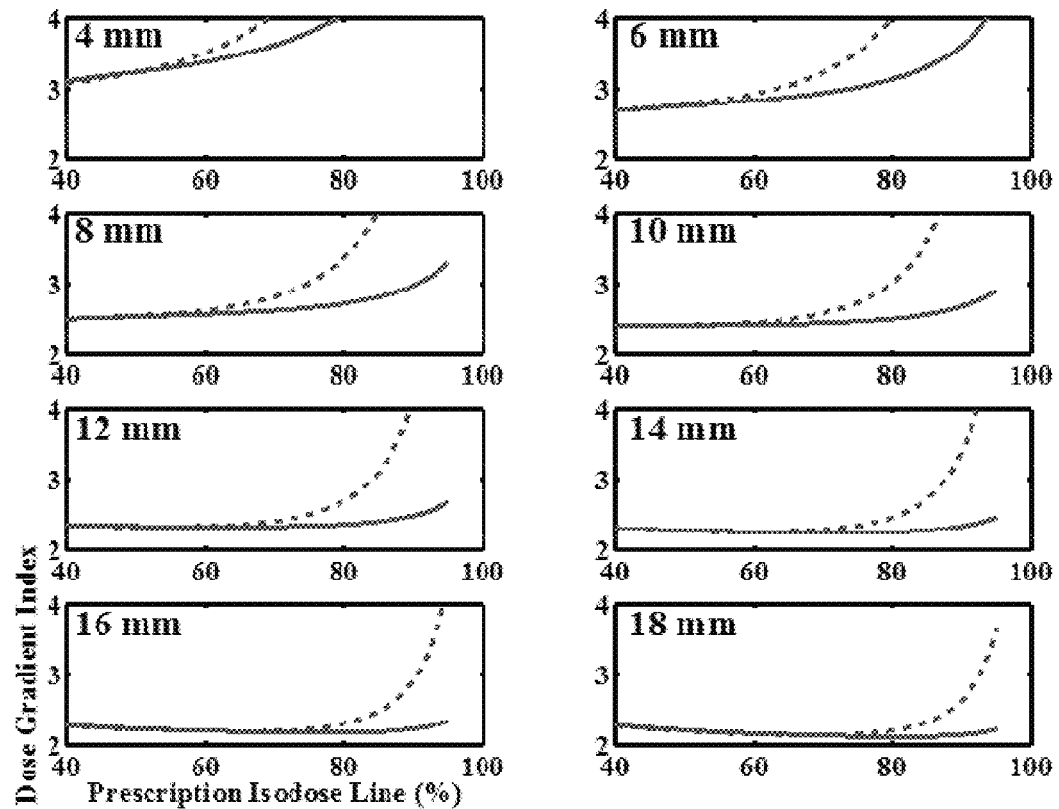
FIG. 9 is a graphical representation of tradeoff curves for various standard and modified collimators in accordance with the present invention.

Referring now to FIGS. 7-9, graphical representations of results from test procedures performed above are provided. In particular, small fields down to 4 mm diameter circular collimators were considered. The fluence distribution was optimized with a fluence and dose grid resolution on the order of 50 µm. FIG. 7 shows theoretical examples of standard and optimized fluence and radial dose distributions taken in a plane perpendicular to the central axis for an 8 mm circular collimator. A first row of results 702 shows the standard and optimized fluence distributions F(r), a second row of results 704 shows the combined kernels $K_S$ and $K_E$ used on both the standard and optimized design and a third row of results 706 shows the standard and optimized dose distributions D(r). The uniformity of the optimized dose distribution D(r) at the third row 706 can be appreciated. Further, the steepness of the dose gradient in the optimized dose distribution D(r), as determined at the distribution between the points where the dose is equal to 80% and 20% of its maximum value, is increased by 29%.

Referring now to FIG. 8, actual dose distributions D(r) that were measured for the standard and modified collimators are illustrated. In particular, a first row of data 802 pertains to the standard collimators without a waveguide in accordance with the present invention and a second row of data 802 pertains to a collimator modified with a channel waveguide in accordance with the present invention. The dose distributions D(r) of the modified collimators at the second row of data 802 have flatter central plateaus in the dose distribution. Further, the dose gradient is increased by 10% for the 4 mm standard collimator prototype and by 8% for the 6 mm standard collimator prototype.

Notably, FIG. 8 demonstrates that modifying the collimators with a channel waveguide in accordance with the systems and methods described above produces sharper dose gradients than those produced by the standard collimators. In particular, such modification entails utilizing an optimized fluence pattern that is implemented as a specifically designed fluence modulator, which is field-size and linac specific. Furthermore, FIG. 8 demonstrates that a more uniform dose distribution can be achieved inside the target volume by implementation of the modification techniques. The techniques use a finer level of modulation than that which is achievable with multileaf collimators or standard compensators. Further, it is noted that both the dose gradient and field dose uniformity are key parameters in the radiosurgery treatment planning for patients and lend to improved quality of the same.

Referring now to FIG. 9, an analysis of tradeoffs between a dose gradient index on the axis y and a prescription isodose line percentage on the axis x for various collimator sizes is illustrated. The 3-D dose distributions were calculated in an isotropic $4\pi$ geometry. Dashed tradeoff curves correspond to standard conical collimators and solid tradeoff curves correspond to optimized conical collimators. It can be seen that the influence of the prescription isodose line on the dose gradient index is reduced with the fluence-optimized collimators as compared to the standard collimators. It is contemplated that as an additional plan quality metric for meningioma treatments, the prescription isodose line at which the dose gradient index is equal to 3 may define a threshold.

Still referring to FIG. 9, it can be seen that the tradeoff between the dose heterogeneity and the dose gradient is less biased at lower prescription isodose lines, that is, more heterogeneous dose distributions, than at higher prescription isodose lines, that is more homogeneous dose. It is contemplated that during clinical treatment planning, a more homogeneous dose distribution may be chosen, in which a number of monitor units MU required is lower than that of a more heterogeneous dose distribution.

It is noted that the graphs of FIGS. 7-9 reflect several simplifications and assumptions that are implicit to the field. First, secondary electrons and photons produced within the custom modulators are not included in the dose calculation. Second, effects on the photon spectrum from the modulator are neglected both in the dose calculations and in the dose measurements with EBT3 film. It is contemplated that some of these considerations can be further addressed in Monte Carlo dose calculations. Furthermore, it is worthy to note that since the fluence modulation in the described method requires some absorption of radiation by the concentric stainless steel shafts, more radiation may be desired to be generated from the radiation source. With recent developments in linac technology, however, the radiation output of accelerators have increased dramatically such that the invention is practicable in linac systems.

The present invention has been described in terms of one or more preferred embodiments, and it should be appreciated that many equivalents, alternatives, variations, and modifications, aside from those expressly stated, are possible and within the scope of the invention.

The invention claimed is:

1. A radiosurgery system, comprising:
a patient table configured to receive a patient thereon;
a radiation source comprising an exit orifice configured to emit a beam of radiation along a path extending from the exit orifice toward the patient table to perform radiosurgery on the patient;
a beam collimator arranged with the path and forming a longitudinal bore extending along the path from an inlet and an outlet; and
a channel waveguide assembly secured to extend along the path to control a portion of the beam of radiation directed through the longitudinal bore of the collimator, the channel waveguide assembly comprising:
a first hollow guide having an inlet orifice and outlet orifice to form a first guide passage through the first hollow guide and defining a first guide inner diameter and a first guide outer diameter, wherein the first guide outer diameter corresponds to the longitudinal bore of the beam collimator;
a second hollow guide having an inlet orifice and outlet orifice to form a second guide passage through the second hollow guide and defining a second guide inner diameter and a second guide outer diameter, wherein the second guide outer diameter is less than the first guide diameter by a predetermined value; and
at least one concentric spacer received around the second hollow guide and having a radial structure configured to correspond to the predetermined value to secure the second hollow guide within the first hollow guide and, thereby, form the channel waveguide configured to constrain the portion of the beam of radiation directed along the path and through the longitudinal bore.

2. The radiosurgery system of claim 1, wherein the radiation source comprises a linear accelerometer.

3. The radiosurgery system of claim 1, wherein the channel waveguide assembly is arranged between the beam collimator and the radiation source and aligned with the longitudinal bore.

4. The radiosurgery system of claim 1, wherein the channel waveguide assembly is arranged within the longitudinal bore and further comprising at least one additional concentric spacer configured to secure the channel waveguide assembly within the longitudinal bore.

5. The radiosurgery system of claim 1, wherein the at least one concentric spacer is compressed between the longitudinal bore and the channel waveguide.

6. The radiosurgery system of claim 1, wherein the at least one concentric spacer comprises a material transparent to the beam of radiation.

7. The radiosurgery system of claim 1, wherein the at least one concentric spacer is friction-fitted between the first hollow guide and the second hollow guide.

8. The radiosurgery system of claim 1, wherein the channel waveguide is removably fixed to an interior surface of the longitudinal bore.

9. The radiosurgery system of claim 1, wherein the channel waveguide comprises a plurality of hollow guides and concentric spacer pairs nested together by decreasing inner diameters.

10. The radiosurgery system of claim 9, wherein at least one of the plurality of hollow guides and concentric spacer pairs is separably nested within a different hollow guide of the channel waveguide.

11. The radiosurgery system of claim 9, wherein the plurality of hollow guides and concentric spacer pairs comprise varying thicknesses of the hollow guides.

12. The radiosurgery system of claim 9, wherein the plurality of hollow guides and concentric spacer pairs comprise varying lengths of the hollow guides.

13. The radiosurgery system of claim 9, wherein the plurality of hollow guides and concentric pairs comprises varying radial thicknesses of the concentric spacers.

14. The radiosurgery system of claim 1, wherein the at least one concentric spacer is removably received around the second hollow guide.

15. The radiosurgery system of claim 1, wherein the first and second hollow guide form one of a hollow cylinder and a hollow cone.

16. The radiosurgery system of claim 1, wherein the first and second hollow guide comprise a material opaque to the beam of radiation.

17. A system for retrofitting a beam collimator, the system comprising:
a plurality of channel waveguide assemblies configured to be operatively associated with respective beam collimators having varying longitudinal bore diameters;
wherein the plurality of channel waveguide assemblies further comprises a plurality of hollow guides and concentric spacers, wherein the plurality of hollow guides and concentric spacers comprise varying inner diameters that are configured to be securably nested together by decreasing inner diameters and secured within the longitudinal bores of the respective beam collimators.

18. The system of claim 17, wherein each of the plurality of hollow guides comprises an outer diameter that operatively corresponds to an inner diameter of at least two of the plurality of concentric spacers.

19. A method for providing a channel waveguide assembly for a beam collimator, comprising:
computing a desired fluence distribution to produce a dose distribution that approximates a top-hat distribution within a desired tolerance, wherein computing the desired fluence distribution includes reducing a sum of squared differences between a calculated dose distribution and a top-hat distribution by adjusting the fluence distribution;
computing a desired fluence distribution of a solid compensator to reproduce the desired fluence distribution, wherein computing the desired fluence distribution of the solid compensator includes reducing a sum of squared differences between the desired fluence distribution and a calculated fluence distribution of the solid compensator;
adjusting a design of the solid compensator by changing a function of the solid compensator;
selecting at least one of a plurality of variably-sized guides according to the desired design of the solid compensator, the at least one guide configured to be nested within a longitudinal bore of the beam collimator such that the combination of the nested guides and beam collimator produces the desired dose distribution at a target location when a radiation beam is collided.

20. A method for creating a collimation system for a radiation system, the method comprising:
determining a set of outer diameter measurements and a set of heights for a plurality of guides, the determination comprising:
identifying a plurality of inner diameter sizes of a multitude of beam collimators having varying inner diameter sizes;
identifying a plurality of cylindrical heights of a multitude of beam collimators;
creating the set of outer diameter measurements for the plurality of guides, the set of outer diameter measurements having smaller diameters that are configured to be received through the inner diameters of the multitude of beam collimators;
creating the set of cylindrical heights for the plurality of guides, the set of cylindrical heights comprising at least one height that is equal to an identified height in the multitude of beam collimators;
manufacturing a plurality of guides with dimensions corresponding to the determined set of outer diameter measurements and the set of cylindrical heights;
manufacturing a plurality of concentric spacers having inner diameters corresponding to the set of outer diameter measurements of the plurality of guides; and
manufacturing a plurality of concentric spacer having outer diameters corresponding to the identified plurality of inner diameter sizes of the multitude of beam collimators.

* * * * *